(12) United States Patent
Iga et al.

(10) Patent No.: US 7,378,108 B1
(45) Date of Patent: May 27, 2008

(54) PERCUTANEOUS ABSORPTION PREPARATION OF COMPOUND HAVING ANGIOTENSIN II ANTAGONISTIC ACTIVITY

(75) Inventors: Katsumi Iga, Suita (JP); Yasuyuki Suzuki, Nishinomiya (JP); Takehiko Naka, Kobe (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 09/913,516

(22) PCT Filed: Feb. 18, 2000

(86) PCT No.: PCT/JP00/00926

§ 371 (c)(1),
(2), (4) Date: Aug. 15, 2001

(87) PCT Pub. No.: WO00/48634

PCT Pub. Date: Aug. 24, 2000

(30) Foreign Application Priority Data

Feb. 19, 1999 (JP) .................................. 11/042396

(51) Int. Cl.
A61K 9/70 (2006.01)
A61K 31/535 (2006.01)
A61K 47/00 (2006.01)

(52) U.S. Cl. .................. 424/443; 424/449; 514/235.8; 514/784

(58) Field of Classification Search ................ 514/946, 514/947, 235.8, 784; 424/443, 444, 448, 424/449
See application file for complete search history.

(56) References Cited

U.S. PATENT DOCUMENTS

| 5,028,435 A | 7/1991 | Katz et al. ................ 424/484 |
| 5,274,104 A | 12/1993 | Arnaud et al. ............. 548/252 |
| 5,985,915 A | 11/1999 | Frangin et al. ............. 514/469 |
| 6,054,484 A * | 4/2000 | Sekine et al. .............. 514/567 |

FOREIGN PATENT DOCUMENTS

| EP | 0 459 136 | 12/1991 |
| EP | 0 520 423 | 12/1992 |
| EP | 0 573 271 | 12/1993 |
| EP | 0 574 174 | 12/1993 |
| EP | 0 752 249 | 1/1997 |
| EP | 0 879 597 | 11/1998 |
| JP | 62-223118 | 10/1987 |
| JP | 6-73008 | 3/1994 |
| JP | 7-2776 | 1/1995 |
| JP | 7-89857 | 4/1995 |
| JP | 7-330627 | 12/1995 |
| JP | 8-40896 | 2/1996 |
| JP | 9-299445 | 11/1997 |
| JP | 11-35464 | 2/1999 |
| WO | 95/06410 | 3/1995 |
| WO | WO 95/06410 | 3/1995 |
| WO | WO 97/28794 * | 8/1997 |
| WO | WO 98/17315 A | 4/1998 |
| WO | WO 99/15210 A2 | 4/1999 |
| WO | 99/56734 | 11/1999 |
| WO | 99/56735 | 11/1999 |
| WO | 99/586734 | 11/1999 |

OTHER PUBLICATIONS

RxList Monographs, Candesartan Cilexetil, 1999.*
Venkatraman et al, "Skin adhesive and skin adhesion 1. Transdermal drug delivery systems", Biomaterials 19:1119-1136, (1998), Elsevier Science Ltd.

* cited by examiner

Primary Examiner—Johann Richier
Assistant Examiner—Konata M. George
(74) Attorney, Agent, or Firm—Foley & Lardner LLP

(57) ABSTRACT

The present invention provides a percutaneous absorption preparation which comprises a compound having angiotensin II antagonistic activity and which allows the compound to permeate through the skin at a desirable rate for a prolonged period.

25 Claims, No Drawings

PERCUTANEOUS ABSORPTION PREPARATION OF COMPOUND HAVING ANGIOTENSIN II ANTAGONISTIC ACTIVITY

TECHNICAL FIELD

The present invention relates to a percutaneous absorption preparation which comprises a compound having angiotensin II receptor antagonistic activity as an active ingredient and is excellent in the absorption efficiency for continuous absorption of the active ingredient into the body through the skin contacting surface thereof.

BACKGROUND ART

A compound having an angiotensin II receptor antagonistic activity is a drug which exhibits high activity for hypertension by such a mechanism that the compound antagonizes angiotensin II which causes a vasoconstriction action through the angiotensin II receptor on the cellular membrane. This drug is developed as an oral dosage form, and, for mitigating patient's troublesomeness, the drug is administered once after having a meal every morning. However, as is generally in common with oral dosage form, a change of a blood level of the active component with time after administration shows a pattern in which the level reaches the maximum 3-4 hours after administration and then falls. It is of importance to suppress the elevation of blood pressure at night and from bedtime to daybreak and, in order to also expect effective concentration also in the afternoon or at night, a little higher dose should be formulated. However, for this kind of a drug, it is of importance to control a dose and, at a higher dose, a patient experiences a blood drug level higher than that required for the patient, even if it is temporal. Sometimes, there is, a possibility that a higher blood level gives the patient displeasure such as giddiness and wandering. Therefore, for this drug, it is said that an ideal preparation form is a sustained-release absorption preparation, which maintains a blood drug level till the next day with a smaller range of fluctuation, once it has been administered to a patient. In general, a so-called extended-release oral dosage form, although the dosage form is made so that absorption an active component at the early stage after administration can be suppressed, the absorption efficiency of the active component is not necessarily constant within the large range of an alimentary canal, and is especially low in the large intestine. Thus, the retention time of absorption is decided by small intestine passing time (about at most 6 hours), and actually, the expected duration of absorptivity is hard to be obtained.

On the other hand, since an active component can be retained at an administration site for a long time by transdermal administration route, generally it is known that duration of much prolonged absorption can be expected in drugs having high skin permeability such as nitroglycerin or steroids.

In addition, since many patients with hypertensive are old, when they are also suffered from other alimentary canal disorders, sometimes, oral administration of a drug for hypertension may cause inconvenience. Therefore, an effective pharmaceutical preparation for hypertension which can be administered conveniently by an administration route other than oral administration is desired.

DISCLOSURE OF INVENTION

The present invention provides a convenient percutaneous absorption preparation of a compound having angiotensin II antagonistic activity. Further, the present invention provides a percutaneous absorption preparation which allows said compound to permeate through skin at a suitable rate for a long time.

To solve the problem described above, the present inventors have studied intensively. As a result, they have completed a percutaneous absorption preparation which comprises a compound having angiotensin II antagonistic activity. Further, they have also found that said percutaneous absorption preparation can give the skin permeation at a suitable rate for a long time and, as a result, can be maintained an effective blood drug concentration can be maintained for one day or more by administration once without reaching, a high blood drug level which causes a side effect by one administration as compared with oral administration.

That is, the present invention provides:

(1) A percutaneous absorption preparation which comprises a skin contacting base containing a compound having angiotensin II antagonistic activity, and a support;

(2) The preparation as described in the above item (1), wherein the skin contacting base further contains a skin permeability regulator;

(3) The preparation as described in the above item (2), wherein the skin permeability regulator is at least one member selected from fatty acid esters, polyols and nonionic surfactants;

(4) The preparation as described in the above item (2) which comprises a fatty acid ester, a polyol and a nonionic surfactant as the skin permeability regulators;

(5) A percutaneous absorption preparation which comprises a compound having angiotensin II antagonistic activity, a fatty acid ester, a polyol and a nonionic surfactant;

(6) The preparation as described in the above item (1), wherein the compound having angiotensin II antagonistic activity is a non-peptide compound;

(7) The preparation as described in the above item (1), wherein the compound having angiotensin II antagonistic activity is 2-ethoxy-1-[[2'-(1H-tetrazol-5-yl)biphenyl-4-yl]methyl]benzimidazole-7-carboxylic acid or a salt thereof;

(8) The preparation as described in the above item (1), wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate or a salt thereof;

(9) The preparation as described in the above item (1), wherein the compound having angiotensin II antagonistic activity is 2-ethoxy-1-[[2'-(2,5-dihydro-5-oxo-1,2,4-oxadiazol-3-yl)biphenyl-4-yl]methyl]benzimidazole-7-carboxylic acid or a salt thereof;

(10) The preparation as described in the above item (2) which comprises a fatty acid ester as the skin permeability regulator;

(11) The preparation as described in the above item (10), wherein the fatty acid ester is an ester of $C_{10-22}$ carbonic acid and $C_{1-12}$ alkyl alcohol;

(12) The preparation as described in the above item (10), wherein the fatty acid ester is isopropyl myristate, isopropyl palmitate, butyl myristate or diethyl sebacate;

(13) The preparation as described in the above item (10), wherein the fatty acid ester is isopropyl myristate;

(14) The preparation as described in the above item (2) which comprises a polyol as the skin permeability regulator;

(15) The preparation as described in the above item (14), wherein the polyol is ethylene glycol, propylene glycol, 1,3-butylene glycol, polyethylene glycol or glycerin;

(16) The preparation as described in the above item (14), wherein the polyol is propylene glycol;

(17) The preparation as described in the above item (2) which comprises a nonionic surfactant as the skin permeability regulator;

(18) The preparation as described in the above item (17), wherein the nonionic surfactant is a fatty acid amide, a polyol fatty acid ester or a polyglycerol fatty acid ester;

(19) The preparation as described in the above item (17), wherein the nonionic surfactant is a fatty acid amide.

(20) The preparation as described in the above item (19), wherein the fatty acid amide is lauric acid diethanol amide or a material containing the same;

(21) The preparation as described in the above item (20), wherein lauric acid diethanol amide or a material containing the same is palm fatty acid diethanol amide;

(22) The preparation as described in the above item (1) which is a skin patch;

(23) The preparation as described in the above item (10), wherein the amount of the fatty acid ester in the skin contacting base is about 1 to 30% by weight based on the weight of the skin contacting base;

(24) The preparation as described in the above item (14), wherein the amount of the polyol in the skin contacting base is about 1 to 30% by weight based on the weight of the skin contacting base;

(25) The preparation as described in the above item (17), wherein the amount of the nonionic surfactant in the skin contacting base is about 1 to 15% by weight based on the weight of the skin contacting base;

(26) The preparation as described in the above item (1) which further contains an adhesive in the skin contacting base;

(27) The preparation as described in the above item (26), wherein the adhesive is an acrylic adhesive;

(28) The preparation as described in the above item (26), wherein the adhesive is a self cross-linking acrylic adhesive;

(29) A preparation as described in the above item (1), wherein the amount of the compound having angiotensin II antagonistic activity in the skin contacting base is about 0.01 to 70% by weight based on the weight of the skin contacting base;

(30) The preparation as described in the above item (1), wherein the amount of the skin permeability regulator in the skin contacting base is about 0 to 70% by weight based on the weight of the skin contacting base;

(31) The preparation as described in the above item (26), wherein the amount of the adhesive in the skin contacting base is about 5 to 99% by weight based on the weight of the skin contacting base;

(32) The preparation as described in the above item (1), wherein the amount of the compound having angiotensin II antagonistic activity per unit of skin contacting area in the skin contacting base is about 0.01 to 100 mg/cm$^2$;

(33) The preparation as described in the above item (1) which maintains effective concentration of the compound having angiotensin II antagonistic activity in blood for one day or more;

(34) A method of preventing and/or treating angiotensin II-mediated diseases which comprises administrating a percutaneous absorption preparation comprising a skin contacting base containing a compound having angiotensin II antagonistic activity and a support;

(35) The method as described in the above item (34), wherein the skin contacting base comprises a skin permeability regulator;

(36) The method as described in the above item (35), wherein the skin contacting base further contains, a fatty acid ester, a polyol, and a nonionic surfactant as the skin permeability regulator;

(37) A method of preventing and/or treating diseases mediated by angiotensin II which comprises administrating a compound having angiotensin II antagonistic activity and a percutaneous absorption preparation comprising fatty acid ester, polyol and nonionic surfactant;

(38) A method of percutaneous absorption of a compound having angiotensin II antagonistic activity which comprises adding a compound having angiotensin II antagonistic activity to a percutaneous absorption preparation comprising a skin contacting base and a support;

(39) A method of regulating percutaneous absorption of a compound having angiotensin II antagonistic activity, which comprises adding a fatty acid ester, a polyol and a nonionic surfactant to a percutaneous absorption preparation comprising the compound having angiotensin II antagonistic activity; and,

(40) Use of a fatty acid ester, a polyol and a nonionic surfactant for regulating percutaneous absorption of a compound having angiotensin II antagonistic activity.

In the present specification, the angiotensin II antagonistic activity is to inhibit competitively or non-competitively binding of angiotensin II to the angiotensin II receptors on the cellular membrane so as to reduce potent vasoconstrictive action or vascular smooth muscle proliferation action induced by angiotensin II and to ameliorate the symptom of hypertension.

The compound having angiotensin II antagonistic activity to be used for the present invention may be either a peptide compound or a non-peptide compound. In view of the advantage of long action, a non-peptide compound having angiotensin II antagonistic activity is preferable. As the compound having angiotensin II antagonistic activity, a compound having an oxygen atom in its molecule is preferable, a compound having an ether linkage or a carbonyl group (said carbonyl group may form a hydroxy group by resonance) is more preferable, a compound having an ether linkage or a ketone derivative is further preferable, and in particular, an ether derivative is preferable.

Any non-peptide compound having angiotensin II antagonistic activity can be used for the present invention. Examples of said compounds include imidazole derivatives disclosed in Japanese Patent Unexamined Publication No. 71073/1981, Japanese Patent Unexamined Publication No. 71074/1981, Japanese Patent Unexamined Publication No. 98270/1982, Japanese Patent Unexamined Publication No. 157768/1983, U.S. Pat. No. 4,355,040, U.S. Pat. No. 4,340, 598, etc.; modified imidazole derivatives disclosed in EP-253310, EP-291969, EP-324377, EP-403158, WO-9100277, Japanese Patent Unexamined Publication No. 23868/1988, Japanese Patent Unexamined Publication No. 117876/1989, etc.; pyrrole, pyrazole and triazole derivatives disclosed in U.S. Pat. No. 5,183,899, EP-323841, EP-409332, Japanese Patent Unexamined Publication No. 287071/1989, etc.; benzimidazole derivatives disclosed in U.S. Pat. No. 4,880,804, EP-0392317, EP-0399732, EP-0400835, EP-425921, EP-459136, Japanese Patent Unexamined Publication No. 63264/1991, etc.; azaindene derivatives disclosed in EP-399731, etc.; pyrimidone derivatives disclosed in EP-407342, etc.; quinazoline derivatives disclosed in EP-411766, etc.; xanthine derivatives disclosed in EP-430300, etc.; fused imidazole derivatives disclosed in EP-434038, etc.; pyrimidinedione derivatives disclosed in EP-442-473, etc.; thienopyridone derivatives disclosed in EP-443568, etc.; heterocyclic compounds disclosed in EP-445811, EP-483683, EP-518033, EP-520423, EP-588299, EP-603712, etc. In addition, their representative compounds are described in Journal of Medicinal Chemistry, Vol. 39, No. 3, pages 625-656 (1996). As the non-peptide compound having angiotensin II antagonistic activity, any one in addition to the compounds described in the above-described references can be employed as far as it has angiotensin II antagonistic activity. Among others, Losartan (DuP753), Eprosartan (SK&F108566), Candesartan cilexetil (TCV-116), Valsartan (CGP-48933), Telmisartan (BIBR277), Irbesartan (SR47436), Tasosartan (ANA-756), their active metabolites (Candesartan, etc.), etc. are preferable.

Preferred examples of the non-peptide compound having angiotensin II antagonistic activity include, for example, a benzimidazole derivative of the formula (I):

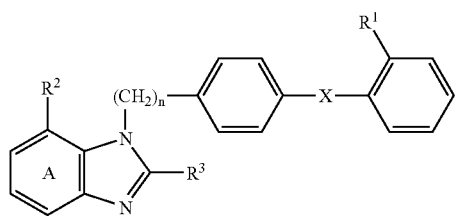

(I)

wherein $R^1$ is a group capable of forming an anion or a group capable of converting thereinto, X shows that the phenylene group and the phenyl group bind to each other directly or through a spacer having an atomic chain length of 2 or less, n is an integer of 1 or 2, the ring A is a benzene ring having an optional substitution, in addition to the group $R^2$, $R^2$ is a group capable of forming an anion or a group capable of converting thereinto, and $R^3$ is an optionally substituted hydrocarbon residue which may bind through a hetero-atom (preferably, an optionally substituted hydrocarbon residue which binds through an oxygen atom), etc., or a salt thereof.

In the above formula (I), the group capable of forming an anion (a group having a hydrogen atom capable of leaving as a proton) as $R^1$ include, for example, (1) a carboxyl group, (2) a tetrazolyl group, (3) a trifluoromethanesulfonic acid amido group (—$NHSO_2CF_3$), (4) a phosphono group, (5) a sulfo group, (6) an optionally substituted 5- to 7-membered (preferably 5- to 6-membered) monocyclic heterocyclic ring residue which contains one or more of N, S and O, etc.

Examples of the above "optionally substituted 5- to 7-membered (preferably 5- to 6-membered) monocyclic heterocyclic ring residue which contains one or more of N, S and O" include

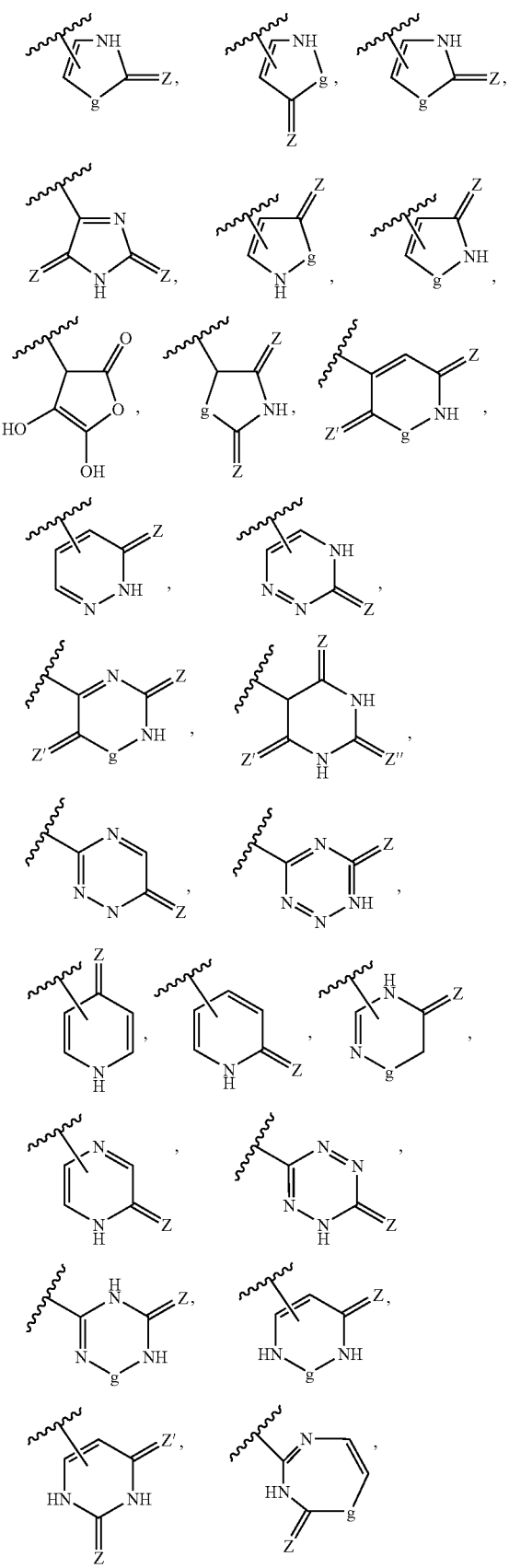

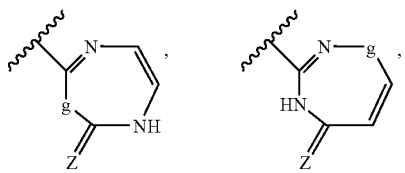

etc. The chemical bond between the heterocyclic ring residue represented by R¹ and the phenyl group to which said heterocyclic ring residue binds may be a carbon-carbon bond as shown above, or a nitrogen-carbon bond via one of the several nitrogen atoms when the symbol g is —NH—, etc. in the above formulas.

For example, when R¹ is represented by the formula:

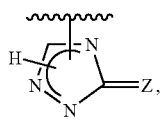

its specific embodiments are

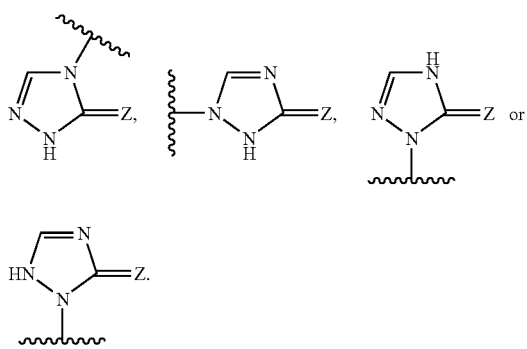

Other examples of R¹ binding through a nitrogen atom include

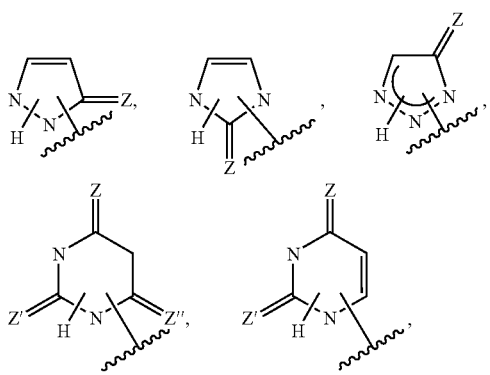

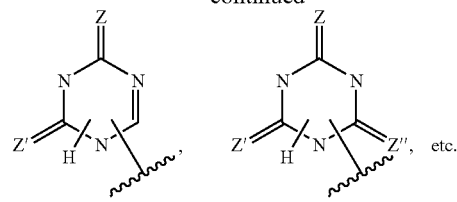

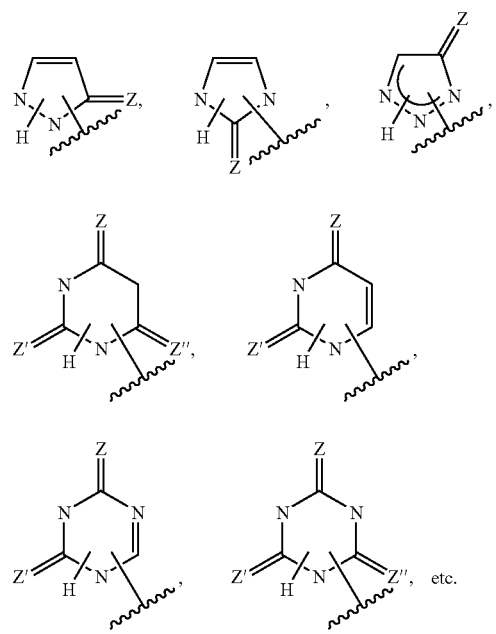

oxidized sulfur atom (e.g., S, S(O), S(O)$_2$, etc.) (preferably a carbonyl group or a thiocarbonyl group, more preferably carbonyl group); and m is an integer of 0, 1 or 2.

Preferred examples of the heterocyclic ring residue represented by R¹ include a heterocyclic ring residue simultaneously having —NH— or —OH group as proton donor and a carbonyl group, a thiocarbonyl group, a sulfinyl group, etc. as proton aceptor, such as an oxadiazolone ring, an oxadiazolothione ring or an thiadiazolone ring, etc.

While the heterocyclic ring residue represented by R¹ may form a condensed ring by connecting the substituents on the heterocyclic ring, it is preferably 5- to 6-membered ring residue, more preferably 5-membered ring residue.

Preferred examples of the heterocyclic ring residue represented by R¹ include a group of the formula:

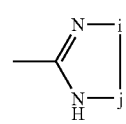

wherein i is —O— or —S—, j is >=O, >=S or >=S(O)m, and m is as defined above (preferably, 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl; more preferably, 2,5-dihydro-5-oxo-1,2,4-oxadiazol-3-yl).

The above-described heterocyclic ring residue ($R^1$) have the following tautomeric isomers. For example, in

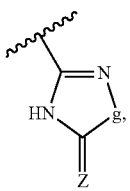

when Z is 0 and g is 0,

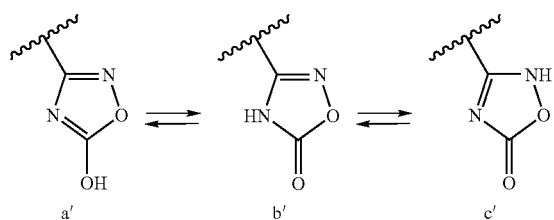

the three tautomeric isomers a', b' and c' exist and a group of the formula:

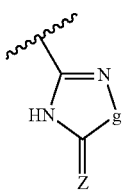

include all of the above a', b' and c'.

The group capable of forming an anion as $R^1$ may be protected by an optionally substituted lower ($C_{1-4}$) alkyl group, an acyl group (e.g., lower ($C_{2-5}$) alkanoyl, benzoyl, etc.) etc. at its possible position.

Examples of the optionally substituted lower ($C_{1-4}$) alkyl group include (1) a lower ($C_{1-4}$) alkyl group optionally substituted with one to three phenyl groups which may have halogen atom, nitro, lower ($C_{1-4}$) alkyl, lower ($C_{1-4}$) alkoxy, etc. (e.g., methyl, triphenylmethyl, p-methoxybenzyl, p-nitrobenzyl, etc.); (2) a lower ($C_{1-4}$) alkoxy-lower ($C_{1-4}$) alkyl group (e.g., methoxymethyl, ethoxymethyl, etc.); (3) a group of the formula: —CH($R^4$)—OCOR$^5$ wherein $R^4$ is (a) a hydrogen, (b) a straight or branched lower $C_{1-6}$ alkyl group (e.g., methyl, ethyl, n-propyl, isopropyl, n-butyl, isobutyl, t-butyl, n-pentyl, isopentyl, neopentyl, etc.), (c) a straight or branched lower $C_{2-6}$ alkenyl group or (d) a $C_{3-8}$ cycloalkyl group (e.g., cyclopentyl, cyclohexyl, cycloheptyl, etc.), and $R^5$ is (a) a straight or branched lower $C_{1-6}$ alkyl group (e.g., methyl, ethyl, n-propyl, isopropyl, n-butyl, isobutyl, sec-butyl, t-butyl, n-pentyl, isopentyl, neopentyl, etc.), (b) a straight or branched lower $C_{2-6}$ alkenyl group, (c) a lower $C_{1-3}$ alkyl group substituted with a $C_{3-8}$ cycloalkyl group (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyl, p-chlorobenzyl, phenethyl, cyclopentylmethyl, cyclohexylmethyl, etc., (d) a lower $C_{2-3}$ alkenyl group substituted with a $C_{3-8}$ cycloalkyl or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as cinnamyl, etc. having an alkenyl moiety such as vinyl, propenyl, allyl, isopropenyl, etc., (e) an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as phenyl, p-tolyl, naphthyl, etc., (f) a straight or branched lower $C_{1-6}$ alkoxy group (e.g., methoxy, ethoxy, n-propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g., allyloxy, isobutenyloxy, etc.), (h) a $C_{3-8}$ cycloalkyloxy group (e.g., cyclopentyloxy, cyclohexyloxy, cycloheptyloxy, etc.), (i) a lower $C_{1-3}$ alkoxy group substituted with a $C_{3-8}$ cycloalkyl (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyloxy, phenethyloxy, cyclopentylmethoxy, cyclohexylmethoxy, etc. having an alkoxy moiety such as methoxy, ethoxy, n-propoxy, isopropoxy, etc., etc.), (j) a lower $C_{2-3}$ alkenyloxy group substituted with a $C_{3-8}$ cycloalkyl (e.g., cyclopentyl, cyclohexyl, cycloheptyl, etc.) or an optionally substituted aryl group (e.g., a phenyl group or a naphthyl group, etc., optionally having a halogen atom, a nitro, a lower ($C_{1-4}$) alkyl, a lower ($C_{1-4}$) alkoxy, etc.) such as cinnamyloxy, etc. having an alkenyloxy moiety such as vinyloxy, propenyloxy, allyloxy, isopropenyloxy, etc. or (k) an optionally substituted aryloxy group (e.g., a phenoxy group, a naphthoxy group, etc., optionally having a halogen atom, a nitro, a lower ($C_{1-4}$) alkyl, a lower ($C_{1-4}$) alkoxy, etc.) such as phenoxy, p-nitrophenoxy, naphthoxy, etc.; etc.

The group capable of forming an anion as $R^1$ may be substituted, in addition to the above protective group such as an optionally substituted lower ($C_{1-4}$) alkyl group or an acyl group (e.g., lower ($C_{2-5}$) alkanoyl, benzoyl, etc.), etc., with an optionally substituted lower ($C_{1-4}$) alkyl group (e.g. an optionally substituted lower ($C_{1-4}$) alkyl group similar to the "optionally substituted lower ($C_{1-4}$) alkyl group" exemplified as a protective group for the above group capable of forming an anion as $R^1$), a halogen atom, a nitro, a cyano, a lower ($C_{1-4}$) alkoxy, an amino optionally substituted with 1 to 2 lower ($C_{1-4}$) alkyl groups, etc., at the possible position.

In the above formula, the group convertible into the group capable of forming an anion (a group having a hydrogen atom capable of leaving as proton) as $R^1$ may be a group convertible into a group capable of forming an anion under biological or physiological conditions (for example, in vivo reaction, etc. such as oxidation, reduction, hydrolysis, etc. by in vivo enzyme, etc.) [so called pro-drug], or the group convertible into a group capable of forming an anion represented by $R^1$ may be a group chemically convertible into a group capable of forming an anion, such as cyano, N-hydroxycarbamimidoyl group (—C(=N—OH)—NH$_2$), a group selected from the class consisting of (1) a carboxyl group, (2) a tetrazolyl group, (3) a trifluoromethanesulfonic acid amido group (—NHSO$_2$CF$_3$), (4) a phosphono group, (5) a sulfo group and (6) an optionally substituted monocyclic 5- to 7-membered (preferably 5- to 6-membered) monocyclic heterocyclic ring residue which contains one or more of N, S and O, each of which is protected with an optionally substituted lower ($C_{1-4}$) alkyl group or an acyl group, etc. [so called synthetic intermediate].

As the group $R^1$, (1) carboxyl, tetrazolyl or 2,5-dihydro-5-oxo-1,2,4-oxadiazol-3-yl (preferably, tetrazolyl), each of which may be protected with an optionally substituted lower ($C_{1-4}$) alkyl (e.g., methyl, triphenylmethyl, methoxymethyl, ethoxymethyl, p-methoxybenzyl, p-nitrobenzyl, etc.) or an acyl group (e.g., lower ($C_{2-5}$) alkanoyl, benzoyl, etc.) or (2) cyano or N-hydroxycarbamimidoyl (preferably cyano) is preferable. Among others, tetrazolyl is preferable.

In the above formula, X shows that the phenylene group is bonded to the adjacent phenyl group directly or through a spacer with an atomic chain of 2 or less (preferably directly). Examples of the spacer with an atomic chain of 2 or less include any divalent chain in which the number of atoms constituting the straight chain is 1 or 2 and which may have a side chain, and specifically lower ($C_{1-4}$) alkylene in which the number of atoms constituting the straight chain is 1 or 2, —CO—, —O—, —S—, —NH—, —CO—NH—, —O—$CH_2$—, —S—$CH_2$—, —CH=CH—, etc.

In the above formula, n is an integer of 1 or 2 (preferably 1).

In the above formula, the ring A may have, in addition to the group $R^2$, another substituent, for example, (1) halogen (e.g., F, Cl, Br, etc.), (2) cyano, (3) nitro, (4) an optionally substituted lower ($C_{1-4}$) alkyl, (5) a lower ($C_{1-4}$) alkoxy, (6) an optionally substituted amino group (e.g., amino, N-lower ($C_{1-4}$) alkylamino (e.g., methylamino, etc.), N,N-di-lower ($C_{1-4}$) alkylamino (e.g., dimethylamino, etc.), N-arylamino (e.g., phenylamino, etc.), alicyclic amino (e.g., morpholino, piperidino, piperazino, N-phenylpiperazino, etc.), etc.), (7) a group of the formula: —CO—D' wherein D' is a hydroxy group or a lower ($C_{1-4}$) alkoxy whose alkyl moiety may be substituted with a hydroxy group, a lower ($C_{1-4}$) alkoxy, a lower ($C_{2-6}$) alkanoyloxy (e.g., acetoxy, pivaloyloxy, etc.), a lower ($C_{1-6}$) alkoxy-carbonyloxy (e.g., methoxycarbonyloxy, ethoxycarbonyloxy, etc.) or a lower ($C_{3-6}$) cycloalkoxycarbonyloxy (e.g., cyclohexyloxycarbonyloxy, etc.), or (8) tetrazolyl, trifluoromethanesulfonic acid amide group, phosphono group or sulfo group, each of which may be protected with an optionally substituted lower ($C_{1-4}$) alkyl ("an optionally substituted lower ($C_{1-4}$) alkyl group" similar to that exemplified as a protective group for the above group capable of forming an anion represented by $R^1$, etc.) or acyl (e.g., lower ($C_{2-5}$) alkanoyl, benzoyl, etc.), etc.

Of these substituents, one or two may simultaneously be present at any possible position on the benzene ring, in addition to the group $R^2$, and preferred examples of the substituents for the benzene ring represented by A include an optionally substituted lower ($C_{1-4}$) alkyl (e.g., a lower ($C_{1-4}$) alkyl, etc. optionally substituted with a hydroxy group, a carboxyl group, a halogen, etc.), a halogen, etc.

As the ring A, a benzene ring having no substituent in addition to the group $R^2$ is preferable.

In the above formula, examples of the group capable of forming an anion (a group having a hydrogen atom capable of leaving as proton) as $R^2$ include (1) an optionally esterified or amidated carboxyl group, (2) a tetrazolyl group, (3) a trifluoromethanesulfonic acid amido group (—$NHSO_2CF_3$), (4) a phosphono group, (5) a sulfo group, etc., each of which may be protected with an optionally substituted lower alkyl group (e.g. an optionally substituted lower ($C_{1-4}$) alkyl group similar to the "optionally substituted lower ($C_{1-4}$) alkyl group" exemplified as a protective group for the above group capable of forming an anion as $R^1$) or an acyl group (e.g., lower ($C_{2-5}$) alkanoyl, benzoyl, etc.), or any one of the groups capable of converting thereinto under biological or physiological conditions (for example, in vivo reaction, etc. such as oxidation, reduction, hydrolysis, etc. by in vivo enzyme, etc.), or chemically.

Examples of the optionally esterified or amidated carboxyl as $R^2$ include a group of the formula: —CO-D wherein D is (1) a hydroxy group, (2) an optionally substituted amino (for example, amino, N-lower ($C_{1-4}$) alkylamino, N,N-di-lower ($C_{1-4}$) alkylamino, etc.) or (3) an optionally substituted alkoxy [e.g., (i) a lower ($C_{1-6}$) alkoxy group whose alkyl moiety is optionally substituted with a hydroxy group, an optionally substituted amino (e.g., amino, N-lower ($C_{1-4}$) alkylamino, N,N-di-lower ($C_{1-4}$) alkylamino, piperidino, morpholino, etc.), a halogen, a lower ($C_{1-6}$) alkoxy, a lower ($C_{1-6}$) alkylthio, a lower ($C_{3-8}$) cycloalkoxy or an optionally substituted dioxolenyl (e.g., 5-methyl-2-oxo-1,3-dioxolen-4-yl, etc.), or (ii) a group of the formula: —O—CH($R^6$)—$OCOR^7$ wherein $R^6$ is (a) a hydrogen, (b) a straight or branched $C_{1-6}$ lower alkyl group (e.g., methyl, ethyl, n-propyl, isopropyl, n-butyl, isobutyl, t-butyl, n-pentyl, isopentyl, neopentyl, etc.), (c) a straight or branched $C_{2-6}$ lower alkenyl group or (d) a $C_{3-8}$ cycloalkyl group (e.g., cyclopentyl, cyclohexyl, cycloheptyl, etc.), and $R^7$ is (a) a straight or branched $C_{1-6}$ lower alkyl group (e.g., methyl, ethyl, n-propyl, isopropyl, n-butyl, isobutyl, sec-butyl, t-butyl, n-pentyl, isopentyl, neopentyl, etc.), (b) a straight or branched $C_{2-6}$ lower alkenyl group, (c) a lower $C_{1-3}$ alkyl group substituted with a $C_{3-8}$ cycloalkyl group (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyl, p-chlorobenzyl, phenethyl, cyclopentylmethyl, cyclohexylmethyl, etc., (d) a lower $C_{2-3}$ alkenyl group substituted with a $C_{3-8}$ cycloalkyl or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as cinnamyl, etc. having an alkenyl moiety such as vinyl, propenyl, allyl, isopropenyl, etc., (e) an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as phenyl, p-tolyl, naphthyl, etc., (f) a straight or branched lower $C_{1-6}$ alkoxy group (e.g., methoxy, ethoxy, n-propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g., allyloxy, isobutenyloxy, etc.), (h) a $C_{3-8}$ cycloalkyloxy group (e.g., cyclopentyloxy, cyclohexyloxy, cycloheptyloxy, etc.), (i) a lower $C_{1-3}$ alkoxy group substituted with a $C_{3-8}$ cycloalkyl (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyloxy, phenethyloxy, cyclopentylmethoxy, cyclohexylmethoxy, etc. having an alkoxy moiety such as methoxy, ethoxy, n-propoxy, isopropoxy, etc., etc.), (j) a lower $C_{2-3}$ alkenyloxy group substituted with a $C_{3-8}$ cycloalkyl (e.g., cyclopentyl, cyclohexyl, cycloheptyl, etc.) or an optionally substituted aryl group (e.g., a phenyl group or a naphthyl group, etc., optionally having a halogen atom, a nitro, a lower ($C_{1-4}$) alkyl, a lower ($C_{1-4}$) alkoxy, etc.) such as cinnamyloxy, etc. having an alkenyloxy moiety such as vinyloxy, propenyloxy, allyloxy, isopropenyloxy, etc. or (k) an optionally substituted aryloxy group (e.g., a phenoxy group, a naphthoxy group, etc., optionally having a halogen atom, a nitro, a lower ($C_{1-4}$) alkyl, a lower ($C_{1-4}$) alkoxy, etc.) such as phenoxy, p-nitrophenoxy, naphthoxy, etc.], etc.

As R², an optionally esterified carboxyl is preferable, and its specific examples include —COOH and a salt thereof, —COOMe, —COOEt, —COOtBu, —COOPr, pivaloyloxymethoxy-carbonyl, 1-(cyclohexyloxycarbonyloxy) ethoxycarbonyl, 5-methyl-2-oxo-1,3-dioxolen-4-yl-methoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy)-ethoxycarbonyl, 1-(isobutyryloxy)ethoxycarbonyl, cyclohexylcarbonyloxymethoxycarbonyl, benzoyloxy-methoxycarbonyl, cinnamyloxycarbonyl, cyclopentyl-carbonyloxymethoxycarbonyl, etc. The group R² may be any one of the groups capable of forming an anion under biological or physiological conditions (for example, in vivo reaction, etc. such as oxidation, reduction, hydrolysis, etc. by in vivo enzyme, etc.), the groups capable of chemically forming an anion (e.g., COO—, its derivative, etc.) or the groups capable of converting thereinto. The group R² may be a carboxyl group or its pro-drug.

Preferred examples of the group R² include a group of the formula: —CO-D wherein D is (1) a hydroxy group or (2) a lower ($C_{1-4}$) alkoxy whose alkyl moiety is optionally substituted with a hydroxy group, an amino, a halogen, a lower ($C_{2-6}$) alkanoyloxy (e.g., acetoxy, pivaloyloxy, etc.), a lower ($C_{3-8}$) cycloalkanoyloxy, a lower ($C_{1-6}$) alkoxy-carbonyloxy (e.g., methoxycarbonyloxy, ethoxycarbonyloxy, etc.), a lower ($C_{3-8}$) cycloalkoxycarbonyloxy (e.g., cyclohexyloxycarbonyloxy, etc.), a lower ($C_{1-4}$) alkoxy or a lower ($C_{3-8}$) cycloalkoxy. Among others, an esterified carboxyl with a lower ($C_{1-4}$) alkyl (preferably, methyl or ethyl) is preferable.

In the above formula, examples of the "hydrocarbon residue" in the "optionally substituted hydrocarbon residue which may bind through a hetero-atom" represented by R³ include (1) an alkyl group, (2) an alkenyl group, (3) an alkynyl group, (4) an cycloalkyl group, (5) an aryl group, (6) an aralkyl group, etc. Among others, an alkyl group, an alkenyl group and a cycloalkyl group are preferable.

Examples of the alkyl group of the above mentioned (1) include straight or branched lower alkyl group having about 1-8 carbon atoms such as methyl, ethyl, propyl, isopropyl, butyl, isobutyl, sec-butyl, t-butyl, pentyl, i-pentyl, hexyl, heptyl, octyl, etc.

Examples of the alkenyl group of the above mentioned (2) include straight or branched lower alkenyl group having about 2-8 carbon atoms such as vinyl, propenyl, 2-butenyl, 3-butenyl, isobutenyl, 2-octenyl, etc.

Examples of the alkynyl group of the above mentioned (3) include straight or branched lower alkynyl group having about 2-8 carbon atoms such as ethynyl, 2-propynyl, 2-butynyl, 2-pantynyl, 2-octynyl, etc.

Examples of the cycloalkyl group of the above (4) include a lower cycloalkyl having about 3-6 carbon atoms, such as cyclopropyl, cyclobutyl, cyclopentyl, cyclohexyl, etc.

Each of the above-described alkyl group, alkenyl group, alkynyl group and cycloalkyl group may be substituted with hydroxy group, an optionally substituted amino group (e.g., amino, N-lower ($C_{1-4}$) alkylamino, N,N-di-lower ($C_{1-4}$) alkylamino, etc.), halogen, lower ($C_{1-4}$) alkoxy group, lower ($C_{1-4}$) alkylthio group, etc.

Examples of the aralkyl group of the above (5) include a phenyl-lower ($C_{1-4}$) alkyl, etc., such as benzyl, phenethyl, etc.

Examples of the aryl group of the above (6) include phenyl, etc.

Each of the above-described aralkyl group and aryl group may be substituted, at any possible position on the benzene ring, with a halogen (e.g., F, Cl, Br, etc.), a nitro, an optionally substituted amino group (e.g., amino, N-lower ($C_{1-4}$) alkylamino, N,N-di-lower ($C_{1-4}$) alkylamino, etc.), a lower ($C_{1-4}$) alkoxy (e.g., methoxy, ethoxy, etc.), a lower ($C_{1-4}$) alkylthio (e.g., methylthio, ethylthio, etc.), a lower ($C_{1-4}$) alkyl (e.g., methyl, ethyl, etc.), etc.

Preferred examples of the "optionally substituted hydrocarbon residue" in the "optionally substituted hydrocarbon residue which may bind through a hetero-atom" represented by R³ include an optionally substituted alkyl or alkenyl group (e.g., a lower ($C_{1-5}$) alkyl or a lower ($C_{2-5}$) alkenyl group, each of which may be substituted with a hydroxy group, an amino group, a halogen, a lower ($C_{1-4}$) alkoxy group, etc.). Among others, a lower ($C_{1-5}$) alkyl (more preferably, ethyl) is preferable.

Preferred examples of the "hetero-atom" in the "optionally substituted hydrocarbon residue which may bind through a hetero-atom" represented by R³ include —O—, —S(O)m- [m is an integer of 0-2], —NR'— [R' is a hydrogen atom or a lower ($C_{1-4}$) alkyl], etc. Among others, —O— is preferable.

Among others, as R³, a lower ($C_{1-5}$) alkyl or a lower ($C_{2-5}$) alkenyl group, each of which may be substituted with a substituent selected from the class consisting of a hydroxy group, an amino group, a halogen and a lower ($C_{1-4}$) alkoxy group and which may bind through —O—, —S(O)m- [m is an integer of 0-2] or —NR'—[R' is a hydrogen atom or a lower ($C_{1-4}$) alkyl], etc. is preferable and a lower ($C_{1-5}$) alkyl or lower ($C_{1-5}$) alkoxy (in particular, ethoxy) is more preferable.

Among the non-peptide compounds having angiotensin II antagonistic activity and represented by the formula (I), a benzimidazole-7-carboxylic acid derivative of the formula (I'):

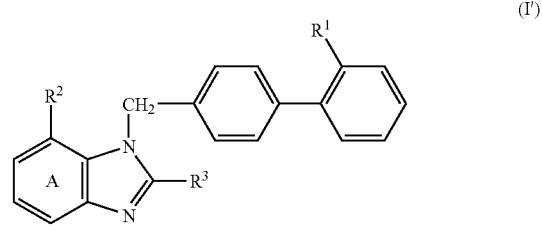

(I')

wherein R¹ is (1) carboxyl group, (2) tetrazolyl group or (3) a group of the formula:

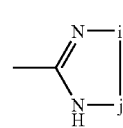

wherein i is —O— or —S—, j is >=O, >=S or >=S(O)m, and m is as defined above; the ring A is a benzene ring having an optional substituent selected from the class consisting of an optionally substituted lower ($C_{1-4}$) alkyl (e.g., a lower ($C_{1-4}$) alkyl optionally substituted with a hydroxy group, a carboxyl group, a halogen, etc.) and a halogen, in addition to the group $R^2$ (preferably, a benzene ring having no substituent in addition to the group $R^2$); $R^2$ is a group of the formula: —CO-D wherein D is (1) a hydroxy group or (2) a lower ($C_{1-4}$) alkoxy whose alkyl moiety may be substituted with a hydroxy group, an amino, a halogen, a lower ($C_{2-6}$) alkanoyloxy (e.g., acetoxy, pivaloyloxy, etc.), a lower ($C_{3-8}$) cycloalkanoyloxy, a lower ($C_{1-6}$) alkoxycarbonyloxy (e.g., methoxycarbonyloxy, ethoxy-carbonyloxy, etc.), a lower ($C_{3-8}$) cycloalkoxycarbonyloxy (e.g., cyclohexyloxycarbonyloxy, etc.), a lower ($C_{1-4}$) alkoxy or a lower ($C_{3-8}$) cycloalkoxy; $R^3$ is a lower ($C_{1-5}$) alkyl or a lower ($C_{2-5}$) alkenyl group, each of which may bind through —O—, —S(O)m- [m is an integer of 0-2] or —NR'— [R' is a hydrogen atom or a lower ($C_{1-4}$) alkyl] and which may be substituted with a substituent selected from the class consisting of a hydroxy group, an amino group, a halogen and a lower ($C_{1-4}$) alkoxy group (preferably, a lower ($C_{1-5}$) alkyl or a lower ($C_{1-5}$) alkoxy; more preferably, ethoxy), etc. or a pharmaceutically acceptable salt thereof is preferable.

Among others, 2-ethoxy-1-[[2'-(1H-tetrazol-5-yl)biphenyl-4-yl]methyl]benzimidazole-7-carboxylic acid[Candesartan], 1-(cyclohexyloxycarbonyloxy)ethyl 2-ethoxy-1-[[2'-(1H-tetrazol-5-yl)biphenyl-4-yl]methyl]benzimidazole-7-carboxylate [Candesartan cilexetil], pivaloyloxymethyl 2-ethoxy-1-[[2'-(1H-tetrazol-5-yl)biphenyl-4-yl]methyl]benzimidazole-7-carboxylate, 2-ethoxy-1-[[2'-(2,5-dihydro-5-oxo-1,2,4-oxadiazol-3-yl)biphenyl-4-yl]methyl]benzimidazole-7-carboxylic acid, or a salt thereof, etc. are preferable.

The above mentioned benzimidazole derivative can be produced by known methods described in, for example, EP-425921, EP-459136, EP-553879, EP-578125, EP-520423, EP-668272, etc. or a method analogous thereto. When Candesartan cilexetil is used for the present invention, a stable C-type crystal described in EP-459136 is preferably used.

The compound having angiotensin II antagonistic activity or a pro-drug thereof may be distinct entity or in the form of any possible pharmaceutically acceptable salts thereof.

Examples of said salts include a salt with inorganic bases (e.g., alkaline metals such as sodium, potassium, etc.; alkaline earth metals such as calcium, magnesium, etc.; transition metal such as zinc, iron, copper, etc.; etc.); organic bases (e.g., organic amines such as trimethylamine, triethylamine, pyridine, picoline, ethanolamine, diethanolamine, triethanolamine, dicyclohexylamine, N,N'-dibenzylethylenediamine, etc.; basic amino acids such as arginine, lysine, ornithine, etc.; etc.); etc., when said compound having angiotensin II antagonistic activity has an acidic group such as a carboxyl group, etc.; and a salt with inorganic acids or organic acids (e.g., hydrochloric acid, nitric acid, sulfuric acid, phosphoric acid, carbonic acid, bicarbonic acid, formic acid, acetic acid, propanoic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.); acidic amino acids such as aspartic acid, glutamic acid, etc.; etc., when said compound having angiotensin II antagonistic activity has a basic group such as an amino group, etc.

The pro-drug of the compound having angiotensin II antagonistic activity [hereinafter, referred to as AII antagonist] means a compound which is converted to AII antagonist under the physiological condition or with a reaction due to an enzyme, an gastric acid, etc. in the living body, that is, a compound which is converted to AII antagonist with oxidation, reduction, hydrolysis, etc. according to an enzyme; a compound which is converted to AII antagonist with gastric acid, etc.; etc.

Examples of the pro-drug of the AII antagonist include a compound wherein an amino group of the AII antagonist is substituted with acyl, alkyl, phosphoric acid, etc. (e.g. a compound wherein an amino group of the AII antagonist is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxy group of the AII antagonist is substituted with acyl, alkyl, phosphoric acid, boric acid, etc. (e.g. a compound wherein an hydroxy group of the AII antagonist is substituted with acetyl, palmitoyl, propanoyl, pivaloyl, succinyl, fumaryl, alanyl, dimethylaminomethylcarbonyl, etc.); a compound wherein a carboxyl group of the AII antagonist is modified with ester, amide, etc. (e.g. a compound wherein a carboxyl group of the AII antagonist is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drug can be produced by per se known method from the AII antagonist.

The pro-drug of the AII antagonist may be a compound which is converted into the AII antagonist under the physiological conditions as described in "Pharmaceutical Research and Development", Vol. 7 (Drug Design), pages 163-198 published in 1990 by Hirokawa Publishing Co. (Tokyo, Japan).

And, the AII antagonist may be hydrate or non-hydrate

Examples of suitable physicochemical properties of the compound having angiotensin II antagonistic activity for the percutaneous absorption preparation include adequate solubility in water (0.005-10 mg/L) and adequate partition ratio in oil (water/octanol partition coefficient: 0.05-10,000) so that a drug is released from the preparation at a suitable rate and distributed to skin and finally absorbed into a systemic circulation.

Other examples of conditions are as follows:

(1) The compound has such a property that it is not destabilized in the preparation;

(2) The compound has such a property that it does not react with any adhesive, any skin permeability regulator, or any generally-used additive which is used in the preparation;

(3) The compound has such a property that it is soluble in a volatile solvent such as alcohol, acetone, ethyl acetate, etc., which is generally used in the production of preparations, in an amount of not less than 0.1 wt %;

(4) The compound has a molecular weight of not higher than about 10,000;

(5) The compound has a melting point of not higher than about 300° C.; and so on.

The percutaneous absorption preparation of the present can be produced according to a generally-used conventional process for production of a percutaneous absorption preparation, or a modification thereof.

As a dosage form in the percutaneous absorption preparation of the present invention, preferred is, for example, a form which is convenient in handling, and has excellent adhesiveness to skin and excellent percutaneous absorbability in occlusive dressing technique. Specifically, it is preferred to employ a form so-called "adhesive" having adhesiveness at room temperature as a base of the skin contacting base. It is preferred to use a patch (skin patch, etc.), etc.

which has an adhesive layer formed on one side of the support (backing layer) from the viewpoint of the easy handling.

Among such percutaneous absorption preparations, for example, a percutaneous absorption preparation which has the skin contacting base comprising the compound having angiotensin II antagonistic activity as the active ingredient is preferred. The skin contacting base is combined with the support (backing layer). One side of the skin contacting base, which is not in contact with the support (backing layer), may be protected with a protection such as a release liner or by being rolled The skin contacting base may not have adhesion. In such a case, the preparation may be fixed with a tape, etc. to be in contact with the skin.

Preferably, said skin contacting base is mainly composed of the compound having angiotensin II antagonistic activity which is an active ingredient, an adhesive and a skin permeability regulator. And the skin contacting base may also contain stabilizers, drug dissolution enhancers, antibiotics, filler, etc. as required.

Preferably, the above-described adhesive is composed of a conventional pharmaceutical adhesive such as (meth) acrylic adhesive, rubber adhesive, silicone adhesive, which has adhesion at room temperature and does not cause a skin rash by hurting corneum when it is brought into contact with the skin. Among them, (meth)acrylic adhesive is most preferred since it does not have chemical reactivity and is qualitatively stable and has excellent air permeability and adhesiveness.

As the above-described (meth)acrylic adhesive, self cross-linking (meth)acrylic copolymer containing soft segments and hard segments may be used. For example, a copolymer, which is obtained by copolymerization of about 50 to about 80% by weight of (meth)acrylate ester and about 20 to about 50% by weight of one or more copolymerizable monomers, is used. As said (meth)acrylate ester, an ester obtained from acrylic acid or methacrylic acid and a primary to tertiary alcohol having 2-18 carbon atoms (preferably 4-12 carbon atoms) may be used.

Specific examples of the (meth)acrylic adhesive include copolymers of 2-hexyl acrylate and acrylic acid, those of 2-ethylhexyl acrylate and hydroxyethyl acrylate, those of 2-ethylhexyl acrylate and vinyl pyrrolidone, those of 2-ethylhexyl acrylate and 2-methoxyethyl acrylate, those of 2-ethylhexyl acrylate, vinyl pyrrolidone and acrylic acid, etc.

As the natural rubber adhesive, natural rubber, synthetic isoprene rubber, polyisobutylene, polyvinyl ether, polyurethane, polybutadiene, styrene-butadiene copolymer, styrene-isoprene copolymer, etc. can be used.

As the silicone adhesive, silicone rubber such as polyorganosiloxane can be used.

One the other hand, as the copolymerizable monomer, the monomer having in its molecule at least one unsaturated double bond which takes part in the copolymerization reaction and in its side chain a functional group such as hydroxy group, carboxyl group, amide group, amino group, etc. can be used.

Examples of the monomers having in its side chain a hydroxy group include 2-hydroxyethyl (meth)acrylate, hydroxypropyl (meth)acrylate, etc.

Examples of the monomers having in its side chain a carboxyl group include α-β unsaturated carboxylic acid such as (meth)acrylic acid, etc.; mono alkyl ester of maleic acid such as butyl maleate, etc.; maleic acid; fumaric acid; crotonic acid; etc.

Examples of the monomers having in its side chain an amide group include alkyl (meth)acrylamide such as acrylamide, dimethylacrylamide, diethylacrylamide, etc.; alkyl ether of methylol(meth)acrylamide such as butoxymethylacrylamide, ethoxymethylacrylamide, etc.; diacetoneacrylamide; vinyl pyrrolidone; etc.

Examples of the monomers having in its side chain an amino group include dimethylamino acrylate, etc.

As the polymerisable monomers, other than the above-described monomers, (meth)acrylonitrile, vinyl acetate, vinyl propionate, N-vinyl-2-pyrrolidone, methyl vinyl pyrrolidone, vinyl pyridine, vinyl piperidone, vinyl pyrimidine, vinyl pyrazine, vinyl pyrrole, vinyl imidazole, vinyl caprolactam, vinyl oxazole, vinyl morpholine, etc. can be used.

One or more of the above mentioned polymerizable monomers may be copolymerized. Preferably, in view of adhesiveness as adhesion property and release property of the compound having angiotensin II antagonistic activity in the skin contacting base, etc., they contains as an essential ingredient at least one monomer selected from carboxyl group-containing monomer and hydroxyl group-containing monomer. And, this monomer is used within a range of about 1 to about 50% by weight, preferably about 3 to about 20% by weight for polymerization with (meth)acrylate ester. If required, the other above exemplified monomer (for example, vinyl monomer such as vinyl acetate or N-vinyl-2-pyrrolidone) may be polymerized with (meth)acrylate ester within a range of less about than 40% by weight, preferably about 30% by weight.

Normally, a copolymer mainly composed of the above-described (meth)acrylate may be prepared by solution polymerization in which the above mentioned monomer is added in the presence of the polymerization initiator. In case of solution polymerization, ethyl acetate or an other polymerization solvent may be added to certain amount of monomers, and they may be reacted in a mixer and a reactor with a reflux condenser, in the presence of the initiator such as an azobis initiator or a peroxide initiator under a nitrogen gas atmosphere at about 70° C. to about 90° C. for about 8 to about 40 hr. And, the monomers may be added all together or in parts.

Preferably, a ratio of (meth)acrylate ester in components of the copolymer mainly composed of the above-described (meth)acrylate ester is more than 50% by weight.

Examples of the above-described azobis initiator include 2,2-azobis-iso-butyronitrile, 1,1'-azobis(cyclohexane-1-carbonitrile), 2,2'-azobis(2,4-dimethylvaleronitrile), etc.

Examples of the above-described peroxide initiator include lauroyl peroxide, benzoyl peroxide, di-tert-butyl peroxide, etc.

As the above-described rubber adhesive, natural rubber, synthetic isoprene rubber, polyisobutylene, polyvinylether, polyurethane, polybutadiene, stylene-butadiene copolymer, stylene-isoprene copolymer, etc. can be used.

As the above-described silicone adhesive, silicone rubber such as polyorganosiloxane, etc. can be used.

The above-described skin permeability regulators are materials which can mainly acts on a corneum which is present on the surface of the skin and enhances and maintain drug permeation through the corneum resulting of control of the drug absorption rate. Any material can be used for the skin permeability regulator in so for as it functions as mentioned above. Preferable, a permeation enhancer through the skin is used for an efficient percutaneous absorption of a drug.

Generally, the corneum is made of multi-layered cellular membranes composed of lipid bilayers which are produced as the result of a metabolism of surface cells, thereby preventing a harmful material from ready permeation into the body. This is a reason why drugs are difficult to be percutaneously absorbed by a normal method. Therefore, a main target of the skin permeability regulator is a lipid bilayer.

As a substance which acts on the lipid bilayer, strong surfactants such as detergents, etc. and solvents such as chloroform, ethers, benzene, etc. are considered. But, they are undesirable since they irritate and destroy lipid bilayer to cause harmful influences.

Examples of desirable properties of the skin permeability regulator are as follows:

(1) The regulator improves fluidity of the lipid bilayer membrane;

(2) The regulator moisturizes gaps of layered structure of membranes, thereby widening the gaps;

(3) The regulator improves solubility of the compound having angiotensin II antagonistic activity in the skin contacting base; etc., and further, (4) The regulator enhances release of the drug from the preparation.

Examples of the regulator (preferably, enhancer), which has these properties and drug releasing property for maintaining an effective blood drug level over a day or more, include the following (A), (B) and (C), etc. The percutaneous absorption preparation of the present invention comprise one or more regulators selected from the following three regulators (A), (B) and (C), preferably three regulators of (A), (B) and (C):

(A) a fat soluble permeability regulator, more preferably fatty acid ester composed of a fatty acid having 6 to 22 carbons and an alcohol having 1 to 12 carbons, etc.

(B) a water soluble permeability regulator, more preferably a polyol, etc.

(C) a nonionic surfactant, more preferably a fatty acid amide such as lauric acid diethanol amide or a material containing it, etc.

Examples of the above-described fatty acids of 6 to 22 carbons include those of 6 to 22 (preferably 10 to 22, more preferably 10 to 20) carbons such as caproic acid, enanthic acid, caprylic acid, capric acid, oleic acid, lauric acid, undecylenic acid, myristic acid, isostearic acid, linolic acid, palmitic acid, margaric acid, stearic acid, hexadecenoic acid, etc.

Examples of the above-described alcohols of 1 to 12 carbons include methyl alcohol, ethyl alcohol, propanol, isopropanol, butanol, t-butanol, hexanol, octanol, etc. Said fatty acid means the same as that above-described fatty acid which is obtained naturally or synthetically.

Thus, examples of the above-described fatty acid ester include isopropyl adipate, isopropyl myristate, diester of sebacic acid, isopropyl palmitate, isopropyl stearate, butyl stearate, octyldodecyl myristate, butyl myristate, hexyl laurate, octyl palmitate, ethyl oleate, etc. Among them, preferred are isopropyl myristate, isopropyl palmitate, butyl myristate, diethyl sebacate, etc. Especially, isopropyl myristate is preferred.

Examples of the above mentioned polyols include low molecular weight glycols such as ethylene glycols (e.g., ethylene glycol, diethylene glycol, triethylene glycol, etc.), glycerin, propylene glycol, 1,3-butylene glycol, etc.; high molecular weight glycols, the molecular weight of which is about 200 to about 6,000, such as polyethylene glycol, polypropylene glycol, etc.; high molecular weight etc. Among them, preferred are ethylene glycol (ethylene glycol, etc.), propylene glycol, polyethylene glycol, 1,3-butylene glycol, glycerin, etc. Especially, propylene glycol is preferred.

Examples of the above-described nonionic surfactant include polyoxyethylene sorbitan fatty acid ester, polyoxyethylene fatty acid ester, polyoxyethylene glyceryl fatty acid ester, polyoxyethylene alkylether, polyoxyethylene alkylarylether, glyceryl monooleate, glyceryl monolaurate, glyceryl monostearate, sorbitan monomyristate, sorbitan monopalmitate, sorbitan monooleate, polyoxyethylene (5) sorbitan monooleate, polyoxyethylene (20) sorbitan monooleate, polyoxyethylene, castor oil derivative, block copolymer type nonionic surfactant (Pluronic L-62, L-64, F-68), etc., polyol fatty acid ester (e.g., glyceryl monooleate, glyceryl monolaurate, glyceryl monostearate, glyceryl monomyristate, glyceryl monopalmitate, glyceryl dioleate, glyceryl dilaurate, glyceryl distearate, glyceryl dimyristate, glyceryl dipalmitate, propylene glycol monocaprylate, caprylic/capric triglyceride, etc.), polyglyceryl fatty acid ester (e.g., triglyceryl fatty acid ester (e.g., triglyceryl oleate, triglyceryl laurate, triglyceryl stearate, triglyceryl myristate, triglyceryl palmitate), tetraglyceryl fatty acid ester (e.g., tetraglyceryl oleate, tetraglyceryl laurate, tetraglyceryl stearate, tetraglyceryl myristate, tetraglyceryl palmitate), pentaglyceryl fatty acid ester (e.g., pentaglyceryl oleate, pentaglyceryl laurate, pentaglyceryl stearate, pentaglyceryl myristate, pentaglyceryl palmitate), hexaglyceryl fatty acid ester (e.g., hexaglyceryl oleate, hexaglyceryl laurate, hexaglyceryl stearate, hexaglyceryl myristate, hexaglyceryl palmitate), heptaglyceryl fatty acid ester (e.g., heptaglyceryl oleate, heptaglyceryl laurate, heptaglyceryl stearate, heptaglyceryl myristate, heptaglyceryl palmitate), decaglyceryl fatty acid ester (e.g., decaglyceryl oleate, decaglyceryl laurate, decaglyceryl stearate, decaglyceryl myristate, decaglyceryl palmitate), etc.), fatty acid amides (oleic acid diethanol amide, myristic acid diethanol amide, stearamidoethyl diethanolamine, vinyl pyrrolidone, lauric acid diethanol amide or a composition including the same (coconut fatty acid diethanol amide, etc.), stearamidoethyl diethylamine, stearamidopropyl dimethylamine, lanolin quaternary ammonium salt, aqueous solution of benzalkonium chloride, etc.), etc. Among them, a fatty acid amide, a polyol fatty acid ester, or a polyglyceryl fatty acid ester is preferred. A fatty acid amide is more preferred. Especially, lauric acid diethanol amide or a material containing the same (a skin permeability regulator including the same), etc. is preferred. In particular, coconut fatty acid diethanol amide, or so on is more preferred.

If required, antioxidants, fillers, drug solubilizing agents, antibiotics reducers of skin irritation, etc. may be added to the preparation of the present invention in addition to the above mentioned additives.

Examples of the above-described antioxidant include vitamin E, vitamin C, etc.

Examples of the above-described filler include china clay, bentonite, titanium dioxide, etc.

Examples of the above-described above described drug solubilizing agent include α-cyclodextrin β-cyclodextrin, γ-cyclodextrin, etc.

Examples of the above-described antibiotics include benzalkonium chloride, benzoic acid, methylparahydroxybenzoate, etc.

Examples of the above-described reducer of skin irritation include silicic anhydride, etc.

Furthermore, other absorbability regulator may also be added. Examples of the other absorbability regulator include polyprenyl azacycloalkane (e.g., 1-dodecylazacycloheptan-2-one, etc.), oil (e.g., olive oil, castor oil, ojoba oil, corn embryo oil, sunflower oil, coconut oil, squalane, squalene, orange oil, and mineral oil, etc.), etc. Preferred skin permeability regulator contains one or more components selected from fatty acid esters, polyols and nonionic surfactants. And, most preferred skin permeability regulator is composed of a fatty acid ester, a polyol and a nonionic surfactant. A preferred fatty acid ester is isopropyl myristate, isopropyl palmitate, butyl myristate, or diethyl sebacate. The most preferred fatty acid is isopropyl myristate. And preferred polyol is ethylene glycol, propylene glycol, 1,3-butylene glycol, polyethylene glycol or glycerin. The most preferred polyol is propylene glycol. And a preferred nonionic surfactant is a fatty acid amide, a polyol fatty acid ester or a poly glycerin fatty acid ester. The most preferred nonionic surfactant is a fatty acid amide. And the most preferred fatty acid amide is lauric acid diethanol amide or a material containing the same.

The most preferred fatty acid amide is coconut fatty acid diethanol amide.

The preparation according to the present invention increases solubility of the compound having angiotensin II antagonistic activity in the skin contacting base, thereby increasing the rate of release from the preparation.

Generally, in case of blending the compound having angiotensin II antagonistic activity to a skin contacting base, a ratio is preferably determined so that the function of skin permeability regulator prevail well and the compound having angiotensin II antagonistic activity is more likely to permeable. For example, (1) The content of the compound having angiotensin II antagonistic activity for the whole skin contacting base is preferably about 0.01% to about 70% by weight, more preferably about 10 to about 60% by weight, further more preferably about 20 to about 50% by weight;

(2) The content of the skin permeability regulator for the whole skin contacting base is preferably about 0% to about 70% by weight (preferably about 1 to about 70% by weight), more preferably about 10 to about 60% by weight, further more preferably about 20 to about 50% by weight;

In case that the skin permeability regulator composed of one or more members selected from a fatty acid ester and a polyol and a nonionic surfactant, a weight ratio of the fatty acid ester, the polyol or the nonionic surfactant in the skin contacting base is preferably 0 to 70% by weight, more preferably 1 to 30% by weight, respectively. Especially, the weight ratio of the fatty acid ester, the polyol or the nonionic surfactant in the skin contacting base is preferably 1 to 30% by weight, 1 to 30% by weight and 1 to 15% by weight, respectively. And, in case that the skin permeability regulator composed of all of the fatty acid ester, the polyol and the nonionic surfactant, a ratio of added polyol is 1/10 to 10 times (more preferably 1/2 to 5 times, most preferably 1) of the weight of the fatty acid ester. And a ratio of added nonionic surfactant is 1/50 to 10 times (more preferably 1/20 to 2 times, most preferably 1/4) of the weight of the added fatty acid ester.

(3) The content of the adhesive for the skin contacting base is about 5 to about 99% by weight (preferably about 5 to about 98% by weight), more preferably about 10 to about 60% by weight, further more preferably about 20 to about 50% by weight.

If required, to the skin contacting base, substances such as the above-described antioxidant, filler, drug solubilizing agent, antibiotics, etc. may be added as other components. These components are used within a range that they do not reduce the adhesion of the skin contacting base and the function of the skin permeability regulator. The amount of them is about 0.01 to about 50% by weight, preferably about 1 to about 20% by weight, more preferably about 1 to about 10% by weight.

A patch, which is an embodiment of the preparation of the present invention, is obtained by fixing a support (backing layer) on one surface of the adhesive layer and fixing a release liner on another surface thereof.

Any support (backing layer) of the patch may be used provided that it can make the skin sweaty by suppressing vaporization of water required for efficient permeation of the active component in the preparation of the present invention after administration and a patient can easily apply the preparation to his or her skin and without feeling incompatibility despite of long-term application (i.e., it has appropriate thickness to apply to the skin). Examples of the support include polyethylene film, polypropylene film, cellulose acetate film, ethyl cellulose film, polyethylene terephthalate film, vinyl acetate-vinyl chloride copolymer film, plastic poly vinyl chloride film, polyurethane film, polyolefin film, and polyvinylidence chloride film, which thickness is about 50 to about 200 μm, and aluminum foil, etc. These may be used as monolayer sheet (film) as well as laminated sheet. And, a woven fabric or a nonwoven fabric may be also used for the support made of a material other than aluminum foil.

The release liner is used as "a cover" for preventing the active components in the percutaneous absorption preparation of the present invention from contamination caused by contacting with other things and from being scraped and loosed before use. Thus, any release liners can be used provided that the patient can peal it off at the time of use, and a condition of the skin contacting base after pealing is maintained to be the same as that before covering with the release liner. Example thereof include siliconized polyethylene terephthalate film, paper, polyester, low-density polyethylene, high-density polyethylene, polypropylene, polystyrene, polyamide, nylon, poly vinyl chloride, etc., which is about 50 to about 100 μm in thickness, are exemplified.

The skin contacting base may be also formed by dissolving a composition comprising the adhesive, the skin permeability regulator and the compound having angiotensin II antagonistic activity in an appropriate solvent; laying the resulting adhesive solution on the support (backing layer); and drying to remove the solvent.

A patch, which is one embodiment of the present invention, is prepared by methods like as follows; a skin contacting base is applied on a support, then a release liner is put on the skin contacting base to form a patch; or a skin contacting base is applied on a release liner, then a support is put on a surface of the skin contacting base. For application of the skin contacting base, each kind of the skin permeability regulators is added to a high concentration solution of the adhesive dissolved in a solvent which is easily volatilized and throughly mixed. Then, the compound having angiotensin II antagonistic activity is also added and throughly mixed to prepare a solution or a dispersion, in which a composition of the skin contacting base is dissolved or dispersed. In this time, as the preferred solvent which is easily volatilized, the solvent which is easily volatilized under appropriate dry conditions (e.g. condition of heating at 50° C. for 1 hour or condition of allowing to stand for 1 day and night at room temperature), and does not remain in an end product (the skin contacting base) and is harmless for living bodies if it remains a little, is selected. For example, ethyl alcohol and a mixed solution composed of ethyl acetate and isopropyl alcohol or acetone within a range of about 0 to about 500% by weight based on that of ethyl acetate are exemplified.

From the viewpoint of increasing efficiency of the application, high concentration of the adhesive in a solvent is preferred. However, in view of homogeneous application, too high concentration of that is undesirable. The concentration to be employed is preferably within a range of about 10% by weight to about 500% by weight, preferably about 20% by weight to about 150% by weight. The concentration of the components other than the adhesive in the composition of the skin contacting base is automatically decided when the concentration of the adhesive is once decided. Preferably, the compound having angiotensin II antagonistic activity is present in a dissolved state as much as possible. Therefore, preferably, the compound is previously dissolved in a solvent which is easily volatilized in a high concentration and then added as a solution in the solvent. Preferred solvents which are easily volatilized include a solvent for dissolving the above mentioned adhesive which does not remain in the dried skin contacting base, as well as acetone, ethyl alcohol, methyl alcohol, etc. This time, among them, acetone or ethyl acetate is preferred. In the concentration of the compound having angiotensin II antagonistic activity in the solvent is selected to be oversaturated or to be similar thereof. The concentration employed is within a range of about 1 to about 20% by weight. When the amount of the compound having angiotensin II antagonistic activity is too large, a part of that is not dissolved. Even in this case, preferably, particles of the compound are microparticles. For this purpose, powders of the compound having angiotensin II antagonistic activity is previously pulverized well, and then dissolved in the solvent.

As the method of application, the following method can be employed: A support (backing layer) or a release liner is fixed on a flat plate which has constant thickness, on which the solution of the skin contacting base composition in the solvent is dropped; and the solution is spread with a roller such as a commercially available applicator (baker applicator: Yoshimitsu Seiki), etc. so that it becomes constant in thickness; and then it is allowed to stand at room temperature for 1 day and night so that the solvent is vaporized. Since heating at 50° C. for 30 minutes in the early phase facilitates rapid vaporization of the solvent, such conditions may be employed for vaporizing the solvent. This is a method for applying a relatively small amount of the solution. For applying a large amount of the solution, a conventional rotating continuous manufacturing apparatus which is improved so as to manufacture a large amount of products can be used. Considering the thickness of the skin contacting base and a volume of the solvent which is calculated from the concentration of the skin contacting base composition, a thickness of the solution of the skin contacting base composition in the solvent to be dropped and spread with the roller is decided so as to be a little larger. The thickness of the skin contacting base is within a range of about 0.01 mm to about 5 mm, preferably about 0.05 mm to about 1 mm. The preparation of the present invention may be previously cut in a size suitable for a particular purpose and used.

A amount of the compound having angiotensin II (AII) antagonistic activity in the preparation of the present invention is not restricted unless blood level of the active component after application and absorption into blood through the skin is less than a concentration at which they causes side effects, and it is enough to maintain an efficient blood level of the active components for a long period. For example, it is within a range of about 0.1 to about 60% by weight, preferably about 0.1 to about 20% by weight, more preferably about 1 to about 10% by weight based on the whole preparation. In case that the preparation of the present invention is a patch, the amount of the compound having angiotensin II antagonistic activity per unit area of skin contacting site is, for example, within a range of about 0.01 to about 100 $mg/cm^2$ (preferably about 1 to about 100 $mg/cm^2$), preferably about 2 to about 50 $mg/cm^2$, more preferably about 5 to about 10 $mg/cm^2$. As the concentration of the compound having angiotensin II antagonistic activity, which is less than the concentration at which they causes side effects but being effective, there can be indicated concentration within the range of about 0.5 to about 1,000 ng/mL, more restricted, about 1 to about 500 ng/mL.

The number of administration (sticking) of the preparation of the present invention is for example 1 to 7 times a week, preferably 3 to 7 times. And, the period of sticking the preparation of the present invention is for example, from half a day to one week, preferably 1 to 3 days. The preparation of the present invention is normally administrated for the period of 1 month to 5 years, and can be prolonged for suppressing progress of the symptom. Preferably, the period is 3 months to 4 years, more preferably 6 months to 2 years. Even such a long-period administration, the preparation of the present invention can be administered to a patient without imposing a burden on him or her.

In case that the preparation of the present invention is a patch or a tape, it may be cut in a size convenient for sticking. And one or more sheets of that may be stuck on same area or multiple area of a body. The area on which the preparation is stuck is not restricted. An area having less body hair (e.g., inside of arm, back, inside of femur) is preferred. Among them, an arm area is preferred.

With low toxicity, the preparation of the present invention can be used in mammals (e.g., human, monkey, sheep, bovine, swine, dog, cat, mouse, rat, hamster, rabbit, etc.) as a safe medicine, etc.

Varying depending on type, content and dosage form of the compound having AII antagonistic activity as the active ingredient; duration of release of the compound having AII antagonistic activity; target disease; subject animal; etc., the dose of the preparation of the present invention is within the range of an effective amount of the compound having AII antagonistic activity. For example, the dose per administration of the active ingredient, the compound having AII antagonistic activity, is preferably chosen within the range from about 0.01 mg to about 10 mg/kg body weight per adult, more preferably from about 0.05 mg to about 5 mg/kg body weight per adult.

The preparation of the present invention is useful as a composition having AII receptor antagonistic activity and can be used for the treatment or prevention of AII-associated diseases such as hypertension, cardiac disease (hypercardia, cardiac insufficiency, myocardial infarction, etc.), nephritis, cerebral apoplexy, etc.

The preparation of the present invention is useful for the prevention or treatment of hypertension, hypercardia, cardiac insufficiency, myocardial infarction, cerebral apoplexy, ischemic peripheral circulation disturbances, myocardial ischemia, vein insufficiency, progressive cardiac insufficiency after myocardial infarction, diabetic complication, diabetic retinopathy, diabetic nephropathy, nephritis, glomerulonephritis, arteriosclerosis, angiohypertrophy, vascular hypertrophy or obstruction after intervention (e.g. percutaneous transluminal coronary angioplasty, etc.), vascular reobstruction after bypass surgery, hyperaldosteronism, glomerulosclerosis, renal insufficiency, glaucoma, intraocular high tension, hyperlipemia, angina pectoris, aneurysm, coronary arteriosclerosis, cerebral arteriosclerosis, peripheral arteriosclerosis, thrombosis, disease of central nervous system, Alzheimer's disease, deficiency of memory, depression, amnesia, senile dementia, sensory disturbances, multiple system organ failure, a disease due to endothelial dysfunction or scleroderma; or for the prevention or amelioration of anxiety neurosis, catatonia, indisposition or dyspeptic symptoms.

The preparation of the present invention can be used in combination with an anti-hypertensive agent (e.g. calcium antagonist, diuretic, β-blocker, diuretic anti-hypertensive agent, etc.) other than the angiotensin II antagonist.

For example, in case of treating a patient (about 60 kg weigh) with hypertension, the preparation of the present invention, which contains the active ingredients of about 1 to about 10% by weight is applied on the inside of his or her arm at bedtime once a day over a month.

BEST MODE FOR CARRYING OUT THE INVENTION

The present invention is hereinafter described in more detail by means of the following Examples, which are not to be construed as limitative.

EXAMPLE

Example 1

TABLE 1

| Composition of skin contacting base | Percentage in skin contacting base |
| --- | --- |
| (Adhesive) | |
| Self cross-linking acrylic copolymer (DuroTAk87-2979) (Skin permeability regulator) | 47.5% |
| Mono lauric acid diethanol amide | 5.0% |
| Isopropyl myristate | 20.0% |
| Propylene glycol | 20.0% |
| (Active ingredients) | |
| 1-cyclohexyloxycarbonyloxy)ethyl 2-ethoxy-1-[[2'-(1H-tetrazol-5-yl)biphenyl-4-yl]methyl]benzimidazole-7-carboxylate | 7.5% |

To a solution of self cross-linking acrylic copolymer (DuroTak87-2979; National Starch & Chemical) dissolved in an ethyl acetate/isopropanol 8:2 (volume ratio) at the concentration of 95% (w/w) were added lauric acid diethanol amide(AminonL-02; KAO Corporation Chemicals), isopropyl myristate, propylene glycol and 1-(cyclohexyloxycarbonyloxy)ethyl, 2-ethoxy-1-[[2'-(1H-tetrazol-5-yl)biphenyl-4-yl]methyl]benzimidazole-7-carboxylate so that their amounts in the whole skin contacting base were 5.0% by weight, 20.0% by weight, 20.0% by weight, and 7.5% by weight, respectively. The mixture solution was blended well. On a siliconized polyethylene terephthalate film 0.075 mm thick (Lintech, 75 μm in thickness, total area including merging area: 600 cm$^2$) spread on a plate of a casting apparatus (Baker applicator: Yoshimitsu seiki), 13 g (containing acetone) of the mixture solution was dropped. Then it was spread with the roller of the apparatus so that the thickness after drying became 0.05 mm, and was air-dried at room temperature for one day. Then, a support (backing layer, polyethylene film, 3M, 76 μm in thickness) was put on the opposite side to a side for contacting with a skin, to prepare a percutaneous absorption preparation of the present invention. When blending the above-mentioned composition, 1-(cyclohexyloxycarbonyloxy)ethyl 2-ethoxy-1-[[2'-(1H-tetrazol-5-yl)biphenyl-4-yl]methyl]benzimidazole-7-carboxylate was previously dissolved in acetone so that its content became 5% by weight and then added. It was confirmed by smelling that solvent for self cross-linking acrylic copolymer (e.g. ethyl acetate, isopropanol) and acetone which was a solvent for dissolving the drug did not exist in the dried preparation.

Example 2

TABLE 2

| Composition of skin contacting base | Percentage in skin contacting base |
| --- | --- |
| (Adhesive) | |
| Self cross-linking acrylic copolymer (DuroTAk87-2979) (Skin permeability regulator) | 47.5% |
| Mono lauric acid diethanol amide | 5.0% |
| Isopropyl myristate | 20.0% |
| Polyethylene glycol600 | 20.0% |
| (Active ingredients) | |
| 1-cyclohexyloxycarbonyloxy)ethyl 2-ethoxy-1-[[2'-(1H-tetrazol-5-yl)biphenyl-4-yl]methyl]benzimidazole-7-carboxylate | 7.5% |

According to the same conditions and method as those in Example 1, the percutaneous preparation of the present invention was obtained except that polyethylene glycol600 was used instead of propylene glycol.

Example 3

TABLE 3

| Composition of skin contacting base | Percentage in skin contacting base |
| --- | --- |
| (Adhesive) | |
| Self cross-linking acrylic copolymer (DuroTAk387-2526) (Skin permeability regulator) | 47.5% |
| Mono lauric acid diethanol amide | 5.0% |
| Isopropyl myristate | 20.0% |
| Polyethylene glycol600 | 20.0% |
| (Active ingredients) | |
| 1-cyclohexyloxycarbonyloxy)ethyl 2-ethoxy-1-[[2'-(1H-tetrazol-5-yl)biphenyl-4-yl]methyl]benzimidazole-7-carboxylate | 7.5% |

According to the same conditions and method as those in Example 2, the percutaneous preparation of the present invention was obtained except that self cross-linking acrylic copolymer DuroTak387-2516 was used instead of self cross-linking acrylic copolymer DuroTak87-2979.

Example 4

TABLE 4

| Composition of skin contacting base | Percentage in skin contacting base |
|---|---|
| (adhesive) | |
| Self cross-linking acrylic copolymer (DuroTAk87-2979) | 87.5% |
| (Skin permeability regulator) | |
| Mono lauric acid diethanol amide | 5.0% |
| (Active ingredients) | |
| 1-cyclohexyloxycarbonyloxy)ethyl 2-ethoxy-1-[[2'-(1H-tetrazol-5-yl)biphenyl-4-yl]methyl]benzimidazole-7-carboxylate | 7.5% |

According to the same conditions and method as those in Example 1, the percutaneous preparation of the present invention was obtained except that one component of lauric acid diethanol amide was used instead of the skin permeability regulator consisting of three components which are lauric acid diethanol amide, isopropyl myristate and propylene glycol.

Example 5

TABLE 5

| Composition of skin contacting base | Percentage in skin contacting base |
|---|---|
| (Adhesive) | |
| Self cross-linking acrylic copolymer (DuroTAk87-2979) | 67.5% |
| (Skin permeability regulator) | |
| Mono lauric acid diethanol amide | 5.0% |
| Propylene glycol | 20.0% |
| (Active ingredients) | |
| 1-Cyclohexyloxycarbonyloxyethyl 2-ethoxy-1-[[2'-(1H-tetrazol-5-yl)biphenyl-4-yl]methyl]benzimidazole-7-carboxylate | 7.5% |

According to the same conditions and method as those in Example 2, the percutaneous preparation of the present invention was obtained except that two components of lauric acid diethanol amide and propylene glycol was used instead of the skin permeability regulator consisting of three components which are lauric acid diethanol amide, isopropyl myristate and propylene glycol.

Example 6

TABLE 6

| Composition of skin contacting base | Percentage in skin contacting base |
|---|---|
| (Adhesive) | |
| Self cross-linking acrylic copolymer (DuroTAk87-2979) | 67.5% |
| (Skin permeability regulator) | |
| Mono lauric acid diethanol amide | 5.0% |
| Isopropyl myristate | 20.0% |
| (Active ingredients) | |
| 1-cyclohexyloxycarbonyloxy)ethyl 2-ethoxy-1-[[2'-(1H-tetrazol-5-yl)biphenyl-4-yl]methyl]benzimidazole-7-carboxylate | 7.5% |

According to the same conditions and method as those in Example 2, the percutaneous preparation of the present invention was obtained except that two components of lauric acid diethanol amide and isopropyl myristate was used instead of the skin permeability regulator consisting of three components which are lauric acid diethanol amide, isopropyl myristate and propylene glycol.

Example 7

TABLE 7

| Composition of skin contacting base | Percentage in skin contacting base |
|---|---|
| (Adhesive) | |
| Self cross-linking acrylic copolymer (DuroTAk87-2852) | 47.5% |
| (Skin permeability regulator) | |
| Mono lauric acid diethanol amide | 5.0% |
| Isopropyl myristate | 20.0% |
| Propylene glycol | 20.0% |
| (Active ingredients) | |
| 1-cyclohexyloxycarbonyloxy)ethyl 2-ethoxy-1-[[2'-(1H-tetrazol-5-yl)biphenyl-4-yl]methyl]benzimidazole-7-carboxylate | 7.5% |

According to the same conditions and method as those in Example 2, the percutaneous preparation of the present invention was obtained except that a self cross-linking acrylic copolymer DuroTak387-2852 which has a larger molecular weight than the self cross-linking acrylic copolymer DuroTak87-2979 used in Example 1 was used instead of it.

Test Example

Seven-week old male SD rats (weight: about 250 g, 4 rats/application group) were anesthetized with ether, and the skins around their abdomens were shaved, and then the rats were turned upward. The percutaneous preparations of the present invention of Examples 1 to 3 which were cut so that their area for sticking became 30 cm$^2$ on the abdomens of the rats. Further, the patches were fixed with stretch bandages so as to prevent pealing off. The calculated amount of 1-(cyclohexyloxycarbonyloxy)ethyl 2-ethoxy-1-[[2'-(1H-tetrazol-5-yl)biphenyl-4-yl]methyl]benzimidazole-7-carboxylate in the applied percutaneous absorption preparations was 20 mg in the percutaneous absorption preparation of Example 1, and. and was 15 mg in that of Example 2

After the preparations were stuck, the rats were brought back into cages under unanesthesia. Blood samples were periodically collected from the tail vein and the concentration of 2-ethoxy-1-[[2'-(1H-tetrazol-5-yl)biphenyl-4-yl]methyl]benzimidazole-7-carboxylic acid, an active metabolite of 1-(cyclohexyloxycarbonyloxy)ethyl 2-ethoxy-1-[[2'-(1H-tetrazol-5-yl)biphenyl-4-yl]methyl]benzimidazole-7-carboxylate in the blood was determined using HPLC.

Extruction of the Drug from the Blood Plasma

Into a 10 mL tube, 0.2 mL of blood plasma 10 mL was poured, and 0.2 mL of 0.2N HCl and 5 mL of diethylether was added. The drug was extracted by shaking with ether, 4.5 mL of the solution in ether was evaporated to dry, and then dissolved in an added eluent for HPLC to be an sample for determining the quantity by HPLC HPLC Conditions column: YMC-Pac ODS eluent: 0.02M $KH_2PO_4/CH_3CN$ (volume ratio 70:30)

flow rate: 1 mL/min detection: UV210 nm

Table 8 shows the average plasma levels of 2-ethoxy-1-[[2'-(1H-tetrazol-5-yl)biphenyl-4-yl]methyl]benzimidazole-7-carboxylic acid at 4, 8, 24, 48 hr after sticking each preparation.

TABLE 8

| Applied sample | 4 hr | 8 hr | 24 hr | 48 hr |
|---|---|---|---|---|
| Percutaneous preparation of Ex. 1 | 130 ng/mL | 280 ng/mL | 800 ng/mL | 170 ng/mL |
| Percutaneous preparation of Ex. 2 | 120 ng/mL | 250 ng/mL | 800 ng/mL | 200 ng/mL |
| Percutaneous preparations of Ex. 2 | 120 ng/mL | 240 ng/mL | 800 ng/mL | 240 ng/mL |

In cases of the percutaneous preparations of Example 1, Example 2 and Example 3, percutaneous absorption of the active components was observed, and a sustention of effective concentration of 2-ethoxy-1-[[2'-(1H-tetrazol-5-yl)biphenyl-4-yl]methyl]benzimidazole-7-carboxylic acid for a prolonged period was confirmed. Moreover, in each administration group, any abnormalities of the skin area on which the preparation was applied, was not observed.

Example 8

According to the same conditions and method as those in Example 3, the percutaneous preparation of the present invention was obtained except that the composition of the skin contacting base contained additional 20% of silicon dioxide and the percent of the total composition was 120%.

Example 9

According to the same conditions and method as those in Example 3, the percutaneous preparation of the present invention was obtained except that each amount of mono lauric acid diethanol amide, isopropyl myristate and polyethylene glycol600 is 10%.

Example 10

According to the same conditions and method as those in Example 9, the percutaneous preparation of the present invention was obtained except that the composition of the skin contacting base contained additional 8.0% of hydrogenated ricinus -50(HCO-50) and the percent of the total composition was 108%.

Example 11

According to the same conditions and method as those in Example 1, the percutaneous preparation of the present invention was obtained except that the composition contains the same amount of 1,3-butylene glycol instead of propylene glycol.

Example 12

According to the same conditions and method as those in Example 1, the percutaneous preparation of the present invention was obtained except that the composition contains the same amount of polyethylene glycol300 instead of propylene glycol.

Example 13

According to the same conditions and method as those in Example 1, the percutaneous preparation of the present invention was obtained except that the composition contains the same amount of isopropyl palmitate instead of isopropyl myristate.

Example 14

According to the same conditions and method as those in Example 1, the percutaneous preparation of the present invention was obtained except that the composition contains the same amount of isopropyl palmitate instead of isopropyl myristate.

Example 15

According to the same conditions and method as those in Example 1, the percutaneous preparation of the present invention was obtained except that the composition contains the same amount of coconut fatty acid ethanol amide instead of mono lauric acid diethanol amide.

Example 16

According to the same conditions and method as those in Example 1, the percutaneous preparation of the present invention was obtained except that the composition contains same amount of 2-ethoxy-1-[[2'-(1H-tetrazol-5-yl)biphenyl-4-yl]methyl]benzimidazole-7-carboxylic acid instead of 1-(cyclohexyloxycarbonyloxy)ethyl 2-ethoxy-1-[[2'-(1H-tetrazol-5-yl)biphenyl-4-yl]methyl]benzimidazole-7-carboxylate.

The present active ingredient was previously dissolved in acetone so that its concentration became 5% and it was used at the time of addition.

Example 17

According to the same conditions and method as those in Example 1, the percutaneous preparation of the present invention was obtained except that the amount of 1-(cyclohexyloxycarbonyloxy)ethyl 2-ethoxy-1-[[2'-(1H-tetrazol-5-yl)biphenyl-4-yl]methyl]benzimidazole-7-carboxylate was 15% by weight.

Example 18

According to the same conditions and method as those in Example 1, the percutaneous preparation of the present invention was obtained except that the amount of lauric acid diethanol amide was 10% by weight.

INDUSTRIAL APPLICABILITY

Using the preparation of the present invention, the compound having angiotensin II antagonistic activity may be absorbed through the skin at desirable rate and the concentration of the drug in blood show less fluctuation compared to oral administration. Moreover, it is convenient to apply the present preparation.

The invention claimed is:

1. A percutaneous absorption preparation which comprises a skin contacting base containing a compound having angiotensin II antagonistic activity and a skin permeability regulator, and a support, wherein the skin permeability regulator comprises a fatty acid ester, a polyol and a nonionic surfactant and wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate.

2. The preparation according to claim 1, wherein the fatty acid ester is an ester of $C_{10-22}$ carboxylic acid and $C_{1-12}$ alkylalcohol.

3. The preparation according to claim 1, wherein the fatty acid ester is isopropyl myristate, isopropyl palmitate, butyl myristate or diethyl sebacate.

4. The preparation according to claim 1, wherein the fatty acid ester is isopropyl myristate.

5. The preparation according to claim 1, wherein the polyol is ethylene glycol, propylene glycol, 1,3-butylene glycol, polyethylene glycol or glycerin.

6. The preparation according to claim 1, wherein the polyol is propylene glycol.

7. The preparation according to claim 1, wherein the nonionic surfactant is a fatty acid amide, a polyol fatty acid ester or a polyglycerol fatty acid ester.

8. The preparation according to claim 1, wherein the nonionic surfactant is a fatty acid amide.

9. The preparation according to claim 8, wherein the fatty acid amide is lauric acid diethanol amide or a material containing the same.

10. The preparation according to claim 9, wherein lauric acid diethanol amide or a material containing the same is palm fatty acid diethanol amide.

11. The preparation according to claim 1, which is a skin patch.

12. The preparation according to claim 1, wherein the amount of the fatty acid ester in the skin contacting base is about 1 to 30% by weight based on the weight of the skin contacting base.

13. The preparation according to claim 1, wherein the amount of the polyol in the skin contacting base is about 1 to 30% by weight based on the weight of the skin contacting base.

14. The preparation according to claim 1, wherein the amount of the nonionic surfactant in the skin contacting base is about 1 to 15% by weight based on the weight of the skin contacting base.

15. The preparation according to claim 1, which further contains an adhesive in the skin contacting base.

16. The preparation according to claim 15, wherein the adhesive is an acrylic adhesive.

17. The preparation according to claim 15, wherein the adhesive is a self cross-linking acrylic adhesive.

18. The preparation according to claim 1, wherein the amount of the compound having angiotensin II antagonistic activity in the skin contacting base is about 0.01 to 70% by weight based on the weight of the skin contacting base.

19. The preparation according to claim 1, wherein the amount of the skin permeability regulator in the skin contacting base is about 0 to 70% by weight based on the weight of the skin contacting base.

20. The preparation according to claim 15, wherein the amount of the adhesive in the skin contacting base is about 5 to 99% by weight based on the weight of the skin contacting base.

21. The preparation according to claim 1, wherein the amount of the compound having angiotensin II antagonistic activity per unit of skin contacting area in the skin contacting base is about 0.01 to 100 mg/cm$^2$.

22. The preparation according to claim 1, which maintains effective concentration of the compound having angiotensin II antagonistic activity in blood for one day or more.

23. A method of treating angiotensin II-mediated diseases which comprises administering topically to a subject in need thereof a percutaneous absorption preparation comprising a skin contacting base containing a compound having angiotensin II antagonistic activity and a skin permeability regulator, and a support, wherein the skin permeability regulator comprises a fatty acid ester, a polyol, and a nonionic surfactant, wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate.

24. A method of percutaneous absorption of a compound having angiotensin II antagonistic activity which comprises adding a compound having angiotensin II antagonistic activity and a skin permeability regulator to a percutaneous absorption preparation comprising a skin contacting base and a support, wherein the skin permeability regulator comprises a fatty acid ester, a polyol, and a nonionic surfactant, wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate.

25. A method of regulating percutaneous absorption of a compound having angiotensin II antagonistic activity, which comprises adding a fatty acid ester, a polyol and a nonionic surfactant to a percutaneous absorption preparation comprising the compound having angiotensin II antagonistic activity, wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate.

* * * * *